US00PP20181P3

(12) United States Plant Patent
Lyrene

(10) Patent No.: US PP20,181 P3
(45) Date of Patent: Jul. 21, 2009

(54) SOUTHERN HIGHBUSH BLUEBERRY PLANT NAMED 'PRIMADONNA'

(50) Latin Name: ***Vaccinium corymbosum* L.**
Varietal Denomination: Primadonna

(75) Inventor: Paul M Lyrene, Gainesville, FL (US)

(73) Assignee: Florida Foundation Seed Producers, Inc., Greenwood, FL (US)

( * ) Notice: Subject to any disclaimer, the term of this patent is extended or adjusted under 35 U.S.C. 154(b) by 701 days.

(21) Appl. No.: 11/288,765

(22) Filed: Nov. 30, 2005

(65) Prior Publication Data

US 2009/0031461 P1 Jan. 29, 2009

(51) Int. Cl.
*A01H 5/00* (2006.01)

(52) U.S. Cl. ..... Plt./157
(58) Field of Classification Search ..... Plt./157
See application file for complete search history.

(56) References Cited

U.S. PATENT DOCUMENTS

PP11,807 P2 * 3/2001 Lyrene ..... Plt./157

OTHER PUBLICATIONS

Internet website: http://www.trueblueplants.com/plants/primadonna–blueberry–plant.html ( 3 pages total).*
Internet website: http://www.trueblueplants.com/plants/jewel–blueberry–plant.html ( 3 pages total).*

* cited by examiner

*Primary Examiner*—Susan B McCormick Ewoldt
(74) *Attorney, Agent, or Firm*—Jondle & Associates, P.C.

(57) ABSTRACT

A new and distinct low-chill southern highbush (*Vaccinium corymbosum*) cultivar. Its novelty lies in the following unique combination of features:

1. Has a low chilling requirement.
2. Has a vigorous bush, between upright and spreading.
3. Produces large berries with excellent scar and firmness.
4. Ripens the first 25% of its berries by April 12 in north Florida in an average year.

4 Drawing Sheets

Latin name of the genus and species: *Vaccinium corymbosum* L.
Variety denomination: 'Primadonna'.

BACKGROUND OF THE INVENTION

The invention relates to a new and distinct variety of southern highbush blueberry (*Vaccinium corymbosum* L.) hybrid named 'Primadonna.' 'Primadonna' is a blueberry clone that is distinguished by its low chilling requirement and by its ability to produce large, firm berries during April and early May when grown in north Florida. Several thousand plants of 'Primadonna' have been propagated by softwood cuttings at Gainesville, Fla., and the resulting plants have all been phenotypically indistinguishable from the original plant. Contrast is made to 'Star' (U.S. Pat. No. 10,675), an important variety widely planted in Florida and Georgia for early-season blueberry production. The new variety is important because it ripens earlier than Star and is more resistant to cane canker (*Botryosphaeria dothidia*).

BRIEF SUMMARY OF THE INVENTION

'Primadonna', when grown in north Florida, is distinguished from all other blueberry plants by the following combination of characteristics: has good resistance to cane canker (*Botryosphaeria corticis*); ripens 9 to 14 days earlier than 'Star'; produces large berries with excellent picking scar and firmness; produces berries in loose clusters which, when mature, detach easily from the stems.

ORIGIN OF THE VARIETY

'Primadonna' originated as a seedling from the cross O'Neal (unpatented)×'FL87-286' (unpatented) made as part of the University of Florida breeding program in a greenhouse in March, 1988. The seedling was first fruited in a high-density field nursery in the spring of 1990. The plant was first asexually propagated by softwood cuttings in June, 1992, and a 10-plant plot was established at the University of Florida Horticultural Unit in Gainesville, Fla. in January 1994. Based on the high fruit quality and early ripening, the plant was subsequently asexually propagated by cuttings and planted at 5 field sites from central Florida to southeast Georgia between 1997 and 2000. A plot of 200 plants established in a commercial field in January, 1999 at Windsor, Fla. has been carefully observed through 6 fruiting cycles. The present invention has been found to retain its distinctive characteristics through successive asexual propagations.

BRIEF DESCRIPTION OF THE DRAWING

The color designations in this specification are from "The Pantone Book of Color" (by Leatrice Eiseman and Lawrence Herbert; Harry N. Abrams, Inc., Publishers, New York, 1990). Where the Pantone color designations differ from the colors in the Drawings, the Pantone colors are the more accurate.

DETAILED BOTANICAL DESCRIPTION

Figure 1:
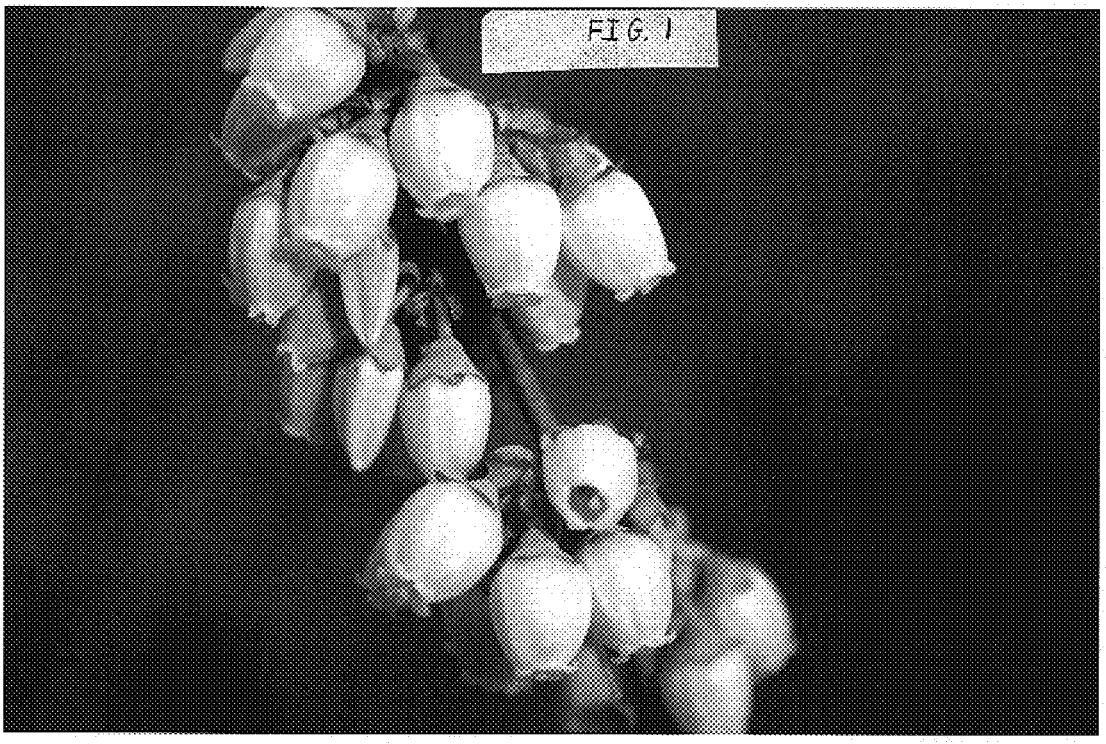
FIG. 1 shows flower clusters of 'Primadonna' during February on a mature plant growing in the field. Cold weather during the flowering period imparts a slight pinkish tinge to the corollas of unopened flowers.
Figure 2:
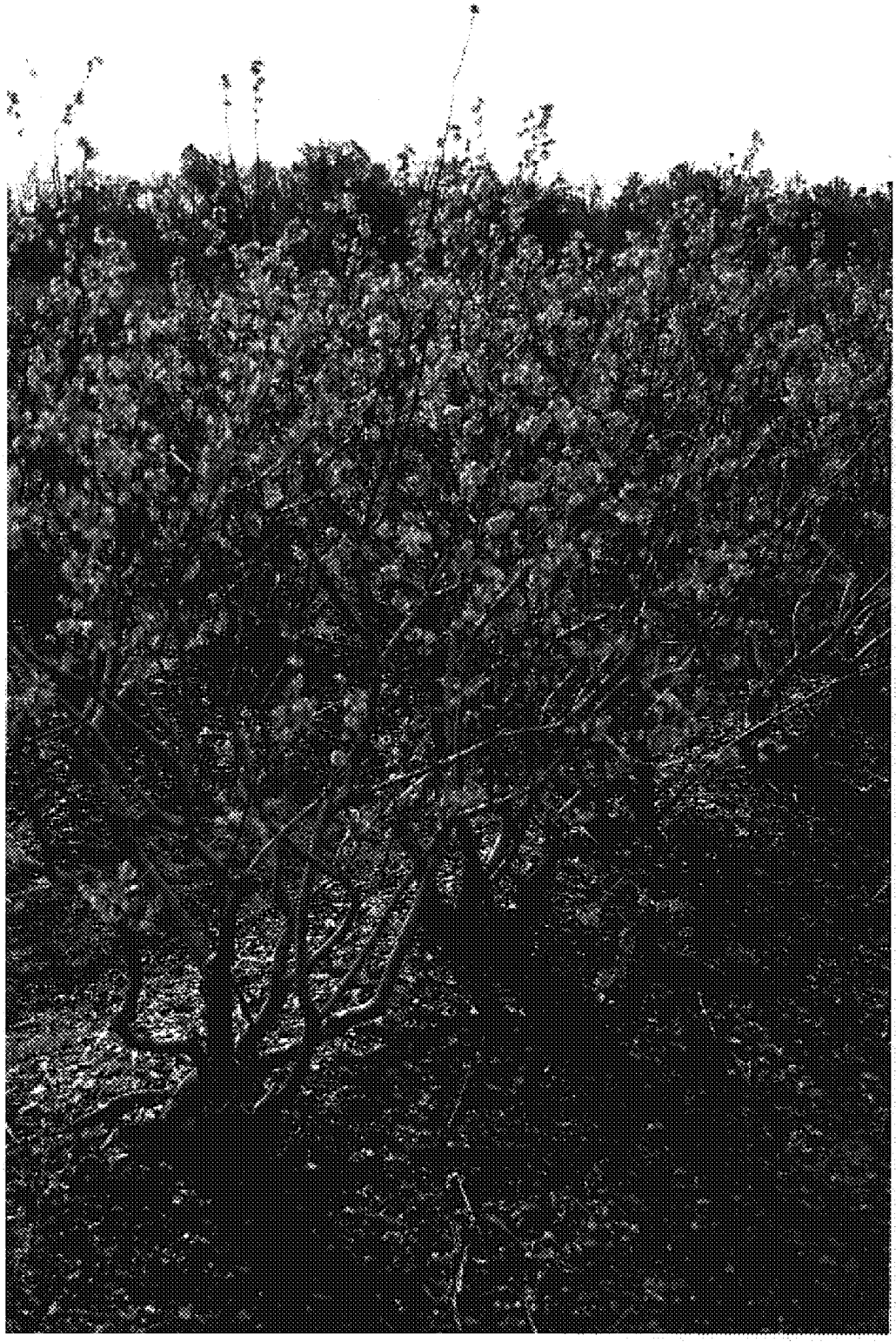
FIG. 2 shows a row of six-year-old plants at the time of flowering in February. The plants are about 2 m tall.
Figure 3:
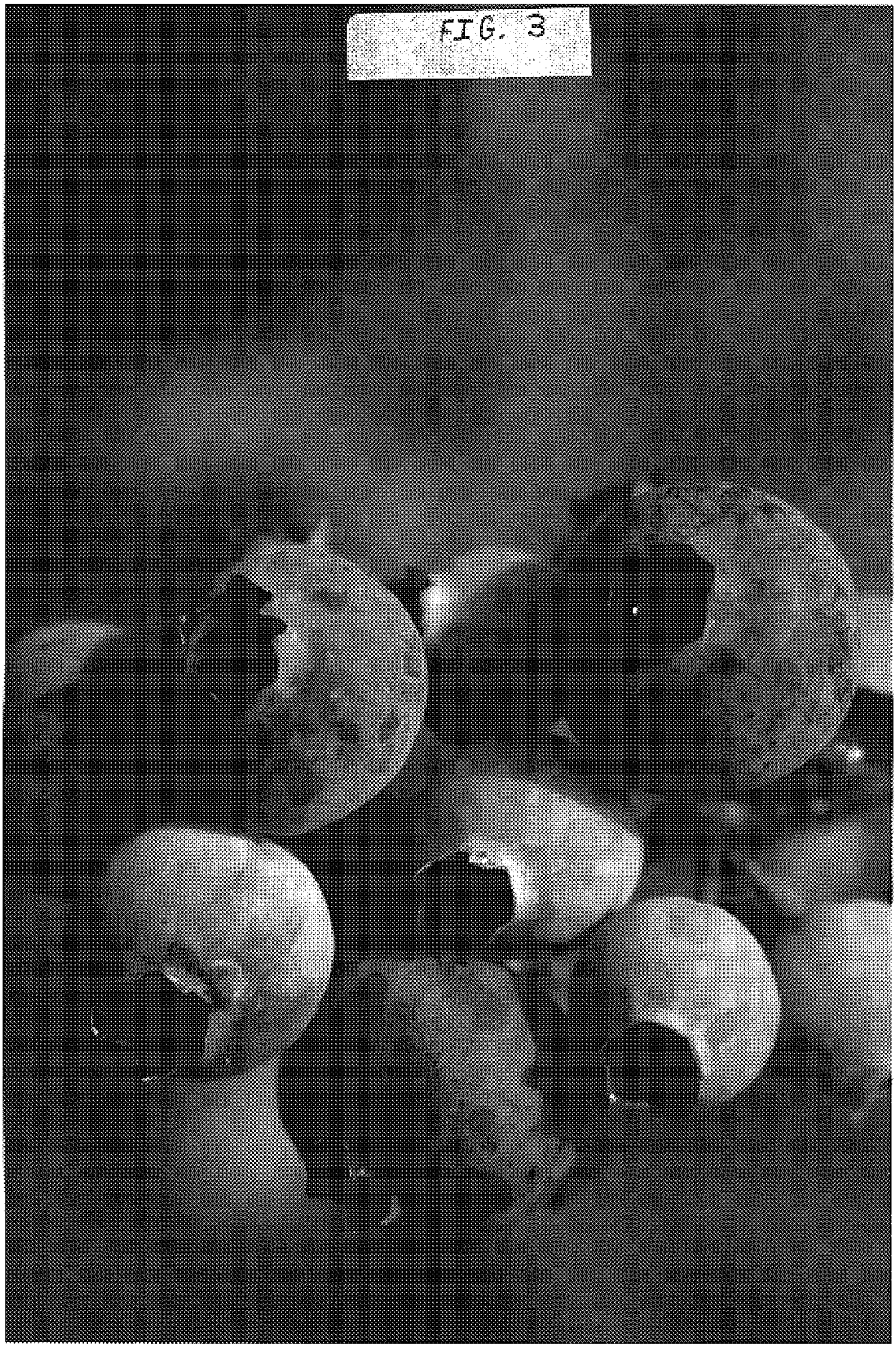
FIG. 3 shows at close range a cluster of berries that is beginning to ripen in the field. Slight frost damage is visible at the calyx end of several berries.
Figure 4:
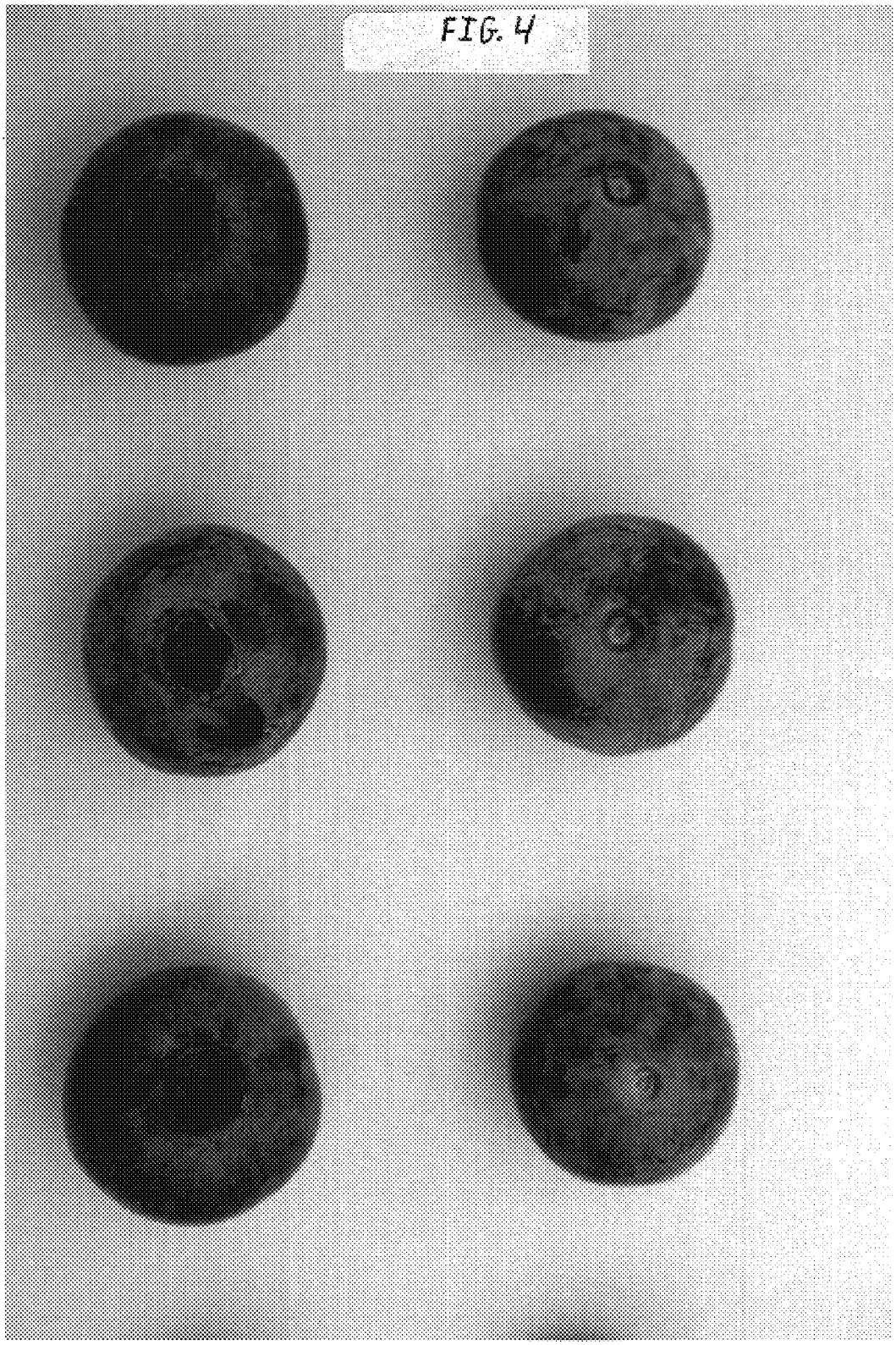
FIG. 4 shows, at close range, the mature berries. The small picking scar and the rather undeveloped calyx lobes can be seen.

MARKET CLASS. 'Primadonna' produces southern highbush blueberries suitable for both the fresh and processed fruit markets.

BUSH. The following descriptions are based on a plot of 200 six-year-old 'Primadonna' plants growing in a test plot in a commercial blueberry planting near Windsor in north Florida.

*Plant height.*—2 m.
*Canopy diameter.*—1.7 m.
*Plant vigor.*—Highly vigorous. Exceeds the vigor of 'O'Neal'.
*Growth habit.*—Between upright and spreading
*Flower bud density (number) along flower twigs in January.*—Medium. Produces more flower buds on upright shoots than 'Star'.
*Twigginess.*—Medium to low. The lateral branches terminate in many small-diameter twigs.

TRUNK AND BRANCHES:
*Trunk diameter.*—The plant typically divides into major canes at a point on the main trunk 10 cm or less above the ground. On plants that have completed three growing seasons in the field, the undivided main trunk below the point of branching (approximately 5 cm above the soil line) averages 5 cm to 8 cm diameter. The largest 3 to 5 principal canes at a point 30 cm above the ground average 2 cm to 4 cm in diameter.
*Suckering tendency.*—Plants have an average of 5 to 7 major canes per plant from a base 30 cm in diameter on 6-year-old plants.
*Surface texture of new wood (9 months old or less) observed in March.*—Smooth.
*Surface texture of strong, 1-year-old shoots observed in March.*—Rough but becoming smooth by exfoliation of rough bark in vertical strips.
*Surface texture of 3-year-old and older wood surface.*—Rough to smooth; continually exfoliating vertical strips of rough bark to leave a smooth surface.
*Color of 1-month-old new shoots observed March 30.*—"Green Moss", Pantone 17-0636.
*Color of previous-summer smooth twigs observed March 30.*—"Pampas", Pantone 14-0826.
*Color of 1-year-old rough bark.*—"Slate Green", Pantone 16-0713.
*Color of 3-year-old rough-textured canes.*—"Cement", Pantone 14-0708.
*Internode length on strong, new shoots measured March 30.*—Mean=1.9 cm.
*Relative time of leafing vs flowering.*—Tends to flower before it begins to leaf when coming out of dormancy. Commercially in north and central Florida, plants are often sprayed with formulations of hydrogen cyanamide in midwinter to enhance early leafing.

MATURE LEAVES:
*Leaf arrangement.*—Alternate.
*Leaf length including petiole, from tip of petiole to end of blade.*—Median is 59 mm.
*Leaf width at widest point.*—Median is 29 mm.
*Leaf shape.*—Elliptic with acute apex and acute base.
*Leaf margin.*—Entire; slightly revolute along the margin of the petiolar half of the blade.
*Color of upper surface of leaves.*—'Juniper', Pantone 18-6330.
*Color of lower surface of leaves.*—'Cameo Green'; Pantone 14-6312.
*Texture of upper surface of leaf blade.*—Smooth and without pubescence.
*Texture of lower surface of leaf blade.*—Smooth and without pubescence.
*Petiole color.*—'Fusia Red', Pantone 18-2328.
*Petiole length.*—5 mm.
*Petiole diameter.*—1 mm to 2 mm.
*Leaf venation pattern.*—One central mid-vein; primary lateral veins pinnate; secondary veins form a reticulate pattern.
*Color of main veins on upper leaf surface.*—'Reed', Pantone 13-0215.
*Color of main veins on lower leaf surface.*—'Fog Green', Pantone 13-0210.
*Pubescence on upper surface of leaves.*—Numerous, very short, white hairs visible at 30X magnification along the midrib. Otherwise glabrous.
*Pubescence on lower surface of leaves.*—None.
*Pubescence on leaf margins.*—None.

FLOWERS:
*Fragrance.*—Faint smell of Camellia flowers.
*Pedicel length at time of anthesis.*—Median=4 mm.
*Peduncle length at time of anthesis.*—Variable; median=11 mm.
*Flower shape.*—Urceolate.
*Pollen staining with 2% acetocarmine.*—This is a measure of potential pollen fertility. 99%.
*Abundance of pollen shed.*—High.
*Color of dried pollen.*—'Yolk yellow', Pantone 14-0846.
*Flower length, pedicel attachment point to corolla tip excluding the pedicel.*—12 mm.
*Length of corolla tube.*—8 to 9 mm.
*Diameter of corolla tube at widest point.*—6 mm.
*Style length.*—Top of ovary to stigma tip. 9 mm.
*Calyx diameter at anthesis.*—Tip of lobe to tip of opposite lobe. 5 mm.
*Corolla aperture diameter.*—3 mm.
*Calyx surface.*—Smooth.
*Corolla color at anthesis.*—'Turtledove', Pantone 12-5202.
*Corolla surface texture.*—Smooth.
*Calyx color at anthesis.*—'Cedar', Pantone 16-0526.
*Pistil color at anthesis.*—'Golden green', Pantone 15-0636.
*Pedicel and peduncle color.*—'Willow green', Pantone 15-0525.
*Flowering period.*—Mean date of 50% open flower at Windsor, Fla. Feb. 16 compared to Feb. 25 for 'Star'.
*Flower cluster (tight, medium, open).*—Medium.
*Number of flowers per cluster.*—Median=7.
*Location of tip of stigma relative to lip of the corolla.*—Stigma tip lacks 1 mm of reaching the end of the corolla tube.

BERRY:
*Mean date of first commercial harvest (25% of fruit ripe) Windsor, Fla.*—April 12.
*Mean date of last commercial harvest.*—May 1.
*Diameter of calyx aperture on mature berry.*—6 mm.

*Calyx lobes on mature berry.*—Size and shape. Small, irregular, not prominent.

*Berry cluster.*—(Tight, medium, or loose). Loose.

*Pedicel length on ripe berry.*—Variable; median length 5 to 6 mm.

*Peduncle length at the time berries are ripe.*—Variable; median length 10 mm.

*Number of ripe berries per cluster.*—Median 6 to 7.

*Mean berry weight on well-pruned plants.*—Mean 2.13 g.

*Mean berry height.*—15 mm.

*Mean berry width.*—17 mm.

*Surface color of ripe berry while on plant.*—"Gull", Pantone 17-3802.

*Surface color of ripe berry after harvest and packing.*—"Gray", Pantone 18-4005.

*Surface color of ripe berry after polishing.*—"Shale", Pantone 19-3903.

*Internal flesh color of ripe berry.*—"White Jade", Pantone 12-0315.

*Berry surface wax.*—How much and how persistent. Medium amount, medium persistence during handling.

*Berry pedicel scar.*—Small and dry.

*Berry firmness.*—High.

*Berry flavor.*—Sweet, low in acidity.

*Berry texture.*—Small seeds, tender skin, not gritty.

*Color of dried seeds.*—'Aztec', Pantone 18-1130.

*Weight of well-developed dried seeds.*—0.47 mg.

*Length of well-developed, dried seeds.*—1.8 mm.

Width of well *-developed, dried seeds.*—1.1 mm.

PHYSIOLOGICAL CHARACTERISTICS:

*Chilling requirement.*—Flower buds break dormancy well after 300 hrs. below 7° C. Spring leafing is best if the plant receives at least 400 hrs. below 7° C.

*Cold hardiness.*—Flowers and fruit hardy to −3° C. The plant, during winter dormancy is hardy to −15° C.

*Regrowth after May hedging.*—Blueberries in north Florida are normally top-pruned mechanically (hedged) shortly after harvest. 'Primadonna' produces an unusually prolific regrowth of new shoots from the top of the bush after May hedging.

*Productivity.*—In northeast Florida, about 5 pounds of berries per bush on plants 4 years old and older.

*Ease of propagation.*—'Primadonna' is easy to propagate from softwood cuttings. Several hundred plants have been propagated by this method in Gainesville, Fla., and all are typical of the variety.

*Pollination requirements.*—Partially self sterile; requires cross pollination with other tetraploid blueberry clones for full fruit set.

RESISTANCE TO DISEASE, INSECTS, MITES:

*Phytophthora root rot.*—High.

*Stem blight* (*Botryosphaeria dothidea*).—Medium to high.

*Cane canker* (*Botryosphaeria corticis*).—High.

*Fungal leaf spots.*—Above average resistance for southern highbush blueberry. Fungicidal control of leaf diseases normally increases yields of southern highbush blueberries where summers are rainy and humid and pathogens are present.

COMPARISON WITH PARENTAL CULTIVARS

'Primadonna' differs from its parent 'O'Neal' in that 'Primadonna' has a lower chilling requirement, has flowers that open earlier in the season, has leaves and stems that are less intensely red in autumn, and has flowers that open more synchronously than 'O'Neal.''Primadonna' differs from its parent 'FL87-286' in that 'Primadonna' is taller, has a more upright growth habit, has flowers that open later in the season, is less evergreen, has larger leaves and berries, and has a looser (more open) berry cluster than 'FL87-286.'

I claim:

1. A new and distinct southern highbush blueberry plant, substantially as illustrated and described, characterized by a vigorous, low-chill bush that produces large berries with excellent scar and firmness during April in north Florida.

* * * * *